(12) United States Patent
Woo

(10) Patent No.: US 7,029,432 B2
(45) Date of Patent: Apr. 18, 2006

(54) TREATMENT OF AFFLICTIONS, AILMENTS AND DISEASES

(76) Inventor: Gilson Woo, 19708 Balan Rd., Rowland Heights, CA (US) 91748

(*) Notice: Subject to any disclaimer, the term of this patent is extended or adjusted under 35 U.S.C. 154(b) by 331 days.

(21) Appl. No.: 10/189,697

(22) Filed: Jul. 3, 2002

(65) Prior Publication Data

US 2003/0009077 A1    Jan. 9, 2003

Related U.S. Application Data

(63) Continuation-in-part of application No. 09/570,510, filed on May 13, 2000, now Pat. No. 6,379,295, and a continuation-in-part of application No. 08/939,429, filed on Sep. 26, 1997, now abandoned.

(51) Int. Cl.
*A61N 1/00* (2006.01)
*A61F 19/00* (2006.01)

(52) U.S. Cl. .......................... 600/15; 128/899

(58) Field of Classification Search .............. 600/9, 600/13–15, 407; 128/898, 899; 324/263; 2/113, 159, 160
See application file for complete search history.

(56) References Cited

U.S. PATENT DOCUMENTS

| | | | | |
|---|---|---|---|---|
| 3,658,051 A | * | 4/1972 | MacLean | 600/14 |
| 4,134,395 A | * | 1/1979 | Davis | 600/407 |
| 5,529,569 A | * | 6/1996 | Woo | 600/9 |
| 5,720,046 A | * | 2/1998 | Lopez et al. | 2/159 |
| 5,782,743 A | * | 7/1998 | Russell | 600/9 |
| 5,950,239 A | * | 9/1999 | Lopez | 2/115 |
| 6,379,295 B1 | * | 4/2002 | Woo | 600/15 |

* cited by examiner

Primary Examiner—Max F. Hindenburg
Assistant Examiner—Nikita R. Veniaminov (57) ABSTRACT

A method and apparatus for alleviating or curing human afflictions, ailments and diseases holistically by application of magnetism. A north pole surface of a magnet is applied to a portion of the extremities, about 990 square inches' of the upper extremities and 1800 square inches of the lower extremities, of a person being treated, and is maintained in contact for a time period or periods in accordance with total flux applied for the afflictions or ailments being treated. The magnet is maintained in contact for a time period or periods sufficient to elicit holistic effect of alleviation or cure and to detect ailments and cure in progress or a balanced treatment point. Magnet is being configurated to accommodate the area being treated and having appropriate total flux.

78 Claims, 4 Drawing Sheets

TREATMENT OF AFFLICTIONS, AILMENTS AND DISEASES

RELATED APPLICATION

This application is a continuation-in-part of application Ser. No. 08/939,429 filed Sep. 26, 1997 by Gilson Woo that is now abandoned and is a continuation-in-part of Ser. No. 09/570,510 filed May 13, 2000 now U.S. Pat. No. 6,379,295 BI issued on Apr. 30, 2002.

BACK GROUND OF THE INVENTION

This invention is a result of a series of findings in my research for magnetic treatment since 1980 from which a method for holistic therapeutic effect of entire body by application of magnetism only to the hands, the head, the neck or the body trunk of patient was either already patented or is in pending by USA Patent Office under the title of Treatment of Ailments, Afflictions and Diseases and the respective U.S. Pat. No. is 5,529,569 Jun. 25, 1996 and U.S. Pat. No. 6,379,295 BI Apr. 30, 2002 and patent application Ser. No. 09/722,239 Apr. 28, 2001 and Ser. No. 09/909,505 Jul. 20, 2001 which are the continuation-in-part of application Ser. No. 08/939,429, filed on Sep. 26, 1997 that is now abandoned by U.S. Pat. No. 6,379,295BI Apr. 30, 2002.

The present invention is directed to a method of applying magnetism only to the extremities of arms and legs of a patient for holistic effect of entire body. The conventional method is holistically effective and applicable to all ailments of human body for concurrent treatment using the hands, head, neck or trunk of the body utilizing meridians of Oriental medical theory and the brain control functions of self-survival healing mechanism.

The upper extremity application utilizing both arms is a method helpful to the neck application of prior art as the arm meridians are run through the neck to the face, and the lower extremity application using both legs is a method helpful to the body trunk application of prior art as the leg meridians are run through the body trunk, neck to the head. However, the upper extremity application is uniquely effective with pains in the region of hand, wrist, elbow, joints, forearm, upper arm, shoulders and related organs and parts along the respective meridian lines that run through the upper extremities which include the meridians of lung, heart, pericardium, large intestine, small intestine and triple warmer. And the lower extremity application is uniquely effective with pains in the region of foot, ankle, lower leg, knee, thigh and related organs and parts along the respective meridian lines that run through the lower extremities which include the meridians of bladder, gall bladder, stomach, pancreas/spleen, liver, kidney and extra meridians of penetrating vessel, yang heel vessel, eum heel vessel, yang linking vessel and eum linking vessel.

The conventional method utilizes only hands, head, neck and trunk of person and the present invention utilizes only extremities of person or combined method with head, neck and trunk in magnetic application. When the extremity application is utilized together with head, neck and trunk magnetic application, effectiveness is increased with far less treatment time and faster healing, especially helpful in relief of chronic type afflictions and pains associated with muscle tension, stiffness, inflammation in the region of extremities and ill-symptoms of the related organs of the body.

This is a method of pain relief and cure for holistic effect of entire body by applying negative magnetic flux, North Pole, only to the extremity portion of the body of the person treated, applying the principles of the Oriental Medicine utilizing the body's meridians known as pathway of life energy of the human body.

This method involves 12 bilateral meridians and 5 extra meridians, and 148 bilateral acupoints that are being disposed through the entire extremities, which are heart of 9 acupoints, pericardium of 8 acupoints, lung of 9 acupoints, small intestine of 9 acupoints, triple warmer of 13 acupoints and large intestine of 14, a total of 62 acupoints for upper extremities, and Bladder of 18 acupoints, Gall Bladder of 14 acupoints, Stomach of 15 acupoints, Kidney of 9 acupoints, Liver of 11 acupoints, Pancreas/Spleen of 11 acupoints and extra meridians of 8 acupoints, a total of 86 acupoints for lower extremities, whereas only hand, head, neck and trunk meridians are being utilized in the referenced prior art.

This method is also extremely effective in relieving pain, inflammation and distress associated with chronic ailments related with the complicated energy systems of the meridians of the extremities of the body. When magnetic fluxes are applied to the extremities as shown in the diagram of FIGS. 3, 4, 5, 6, 7, 8, 9, 10, 11, 12, 13, 14, 15, 16, 17, 18, 19, 20, 22 and 23 of drawings for therapeutical effect, life energy pathways of the extremity meridians are directly affected.

These important elements of the energy flow channels are being stimulated or restored instantly, upon application of magnetism to the extremities, to elicit holistic therapeutical effect of entire body, thus breathing, circulation and energy flow are improved and order and balance of the energy system is restored to help body heals fast and relieves pains effectively, which are all observable and verifiable at sight.

This method enables body to sense responses from ill parts/locations and cure in progress in same way as the head, neck, trunk and two-hand method of the referenced prior art, whereas note there is no response being occurred or detected from the healthy body with no ailments by application of magnetism. This phenomenon is believed to be some form of reaction of brain sick memory recall in response to the magnetic application and further to indicate that, when body is in sickness, pathway of life-energy meridian and sensory neurons of the nervous system are being hindered by some form of blockage and, when the flow is stimulated by magnetic flux, the flow hindrance causes responses and symptoms and, when the body is in health, the pathways are all clear and wide open for free flow thus causing no response or symptom even under magnetically stimulated condition in energy flow and neural transmission. An evidence to support this fact is that, when pain and ailment are cured by magnetic flux, all such responses and symptoms are gone and disappeared. Magnets and magnetism have heretofore been utilized in the treating of human disease and afflictions. Any magnet configurated and sized to cover substantially the treatment area of the extremities can be used for this method as long as it produces a sedative and healing effect in a range of 30 to 250,000 total flux and the North Pole surface is flat and smooth for good contact to the skin of the extremities. Total flux of up to 5,000 is believed to be ideal for pain control and management of sedative effect and total flux of above 5,000 is believed to be good for healing cure effect.

In comparison with the referenced method of prior art, this method of utilizing extremity is more beneficial in some ways: more effective in relieving pains of upper and lower extremities and the organs of related meridians such as lung and large intestine, heart and small intestine, pericardium and triple warmer, liver and gall bladder, kidney and bladder, and digestive systems, and easy of balanced treatment, etc.

Magnetic application in terms of alternative medicine or natural energy medicine has been widely recognized in the Western in recent years although this has been primarily an Oriental practice. Many innovative methods of magnetic treatment have been introduced, yet there is much left to be done for improvement.

Therefore, a general object of the present invention is to provide treatment for a wide variety of ailments and diseases for holistic effects, except for those requiring surgical treatment.

An object of the present invention is to provide such a method which utilizes magnetism applied to a portion of the extremities of a person, thus to provide concurrent treatment of a plurality of ailments and afflictions of the entire body for holistic effect.

An object of the invention is to provide such treatment utilizing magnetism in simplified methods that can be practiced without specialized professional knowledge.

An object of the invention is to provide such methods that provide recovery from fatigue and which provide energetic, vigorous feelings.

An object of the invention is to provide such methods that provide substantial cures, relief of pain and rapid healing.

An object of the invention is to provide such methods that provide breathing control and/or improved circulation of the blood of the person to allow an optimum condition of the body systems.

An object of the invention is to provide methods and techniques of treatment utilizing magnetism, independently of meridians or acupuncture points according to Oriental medicine.

An object of the invention is the provision of such a method that is economical and effective.

An object of the invention is the provision of such methods that, properly utilized, are safe and involve no harm to a patient and no adverse reaction or sequelae.

An object of the invention is the provision of such methods that involve the effecting of a balance of the energy systems of the body, in accordance with Oriental medicine theories, in treating ailments and applications.

An object of the present invention is to provide such a method which utilizes magnetism applied to a portion of the extremities of a person, thus to provide concurrent treatment of a plurality of ailments and afflictions of the entire body for holistic effect.

SUMMARY OF THE INVENTION

The foregoing object and advantages, as well as others which will be apparent from the specification, are achieved by a method for treating and alleviating human afflictions, ailments and diseases by the application of magnetism to a person being treated.

A North Pole surface of a magnet is applied to the person, only to a portion of the extremities.

Contact with magnet is maintained for a sufficient time period or periods to provide substantial alleviation or cure. The magnetic strength or total flux applied to the extremities may typically be from about 30 to about 250,000 total flux. The magnet may be maintained in contact with the person for a time period sufficient for the eliciting of substantial alleviation or cure and to detect ailments and cure in progress or a balanced treatment point. Magnet means are provided for application to the portion of the extremities of a person being treated, with a North Pole surface of the magnet means configurated to engage the portion or the area of the extremities of the person.

DESCRIPTION OF THE PREFERRED EMBODIMENT

According to the present invention magnet or magnets are applied to the extremities of arms and legs of a person being treated. The method of extremity magnetic treatment involves application of magnetism by attaching a magnet directly to the designated treatment area of the extremities of the arms and legs only to elicit holistic therapeutical effect of entire body.

In utilizing the method, where affliction or chronic ailment is treated, the extremities are subjected to the magnetic treatment according to the invention.

The method is an effective and powerful method of holistic treatment.

Figure 1:
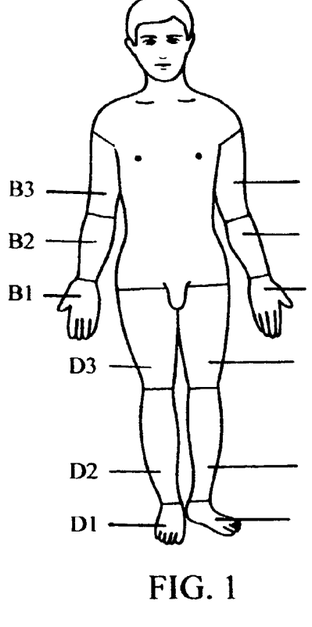
FIG. 1 is a perspective view showing whole designated treating regions utilized in the invention in the application of magnet means to the extremities of a person.
Figure 2:
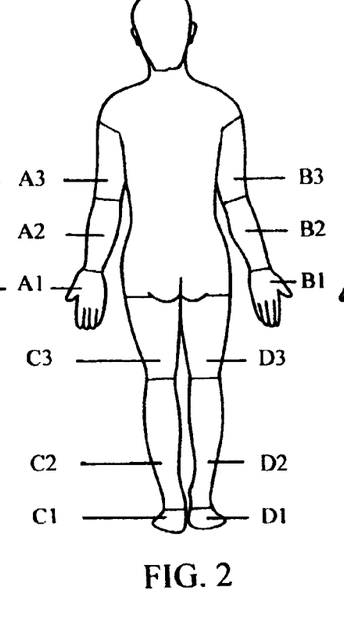
FIG. 2 is a perspective view showing a backside of whole designated treating regions utilized in the invention in the application of magnet means to the extremities of a person.

The affliction, ailments and diseases of the entire body of a person may be treated concurrently by application of magnet means to the area of the extremities of the person. In this method, magnets are applied directly to the designated area of the extremities of a patient. A particular area of the extremities where the meridians are disposed is being designated for holistic therapeutical effect and its size is about 990 square inches for the upper extremities, 33 inches long and 15 inches round for each arm, and about 1800 square inches for the lower extremities, 45 inches long and 20" inches round for each leg, as shown in FIGS. 1 and 2 of the drawing. The designated area of the arms covers from finger tip line in 15 inches round all the way through the hand, wrist, forearm, upper arm to the joint line of the shoulder in 33 inches long. The designated area of the legs covers from toe line in 20" round all the way through the foot, heel, ankle, lower leg, knee, thigh to the joint line of the buttocks/hip in 45" long. The meridians of the lung, heart and pericardium are disposed through outer part of the arms, and the large intestine, small intestine and triple warmer meridians are disposed through inner part of the arms of the body, whereas, the stomach, bladder, gall bladder, penetrating vessel, yang heel vessel and yang linking vessel meridians are disposed through outer part of the legs and pancreas/spleen, kidney, liver, eum heel vessel and eum linking vessel meridians are disposed through inner part of the legs of the body. Thus, there are 6 bilateral meridians and 62 acupoints for each arm, and 6 bilateral meridians, 5 extra meridians and 86 acupoints for each leg that are disposed in the designated area involving the extremity method of holistic treatment.

However, the 62 acupoints in the area of the arms are normally used by acupuncture technics to treat only the ailments associated with local pains of hand, forearm, upper arm and the organs of the related meridians, and the 86 acupoints in the area of the legs are normally used by acupuncture technics to treat only the ailments associated with local pains of foot, leg, thigh and the organs of the related meridians, and they provide no means of holistic effects of entire body.

But by applying magnetism to the area as a whole in accordance with the invention provides an effective means of holistic therapeutical effect of whole body as well as balanced treatment effect.

In order to elicit such a holistic therapeutical effective and balanced treatment, the whole area of the extremities may be divided, as shown in FIGS. 1 and 2, into 4 treating regions such as A & B for upper extremities and C & D for lower extremities respectively for both arms and legs of the body by designating subregions of A-1 for left hand, A-2 for left forearm, A-3 for left upper arm, and B-1 for right hand, B-2 for right forearm, B-3 for right upper arm, and C-1 for left foot, C-2 for left lower leg, C-3 for left thigh, D-1 for right foot, D-2 for right lower leg, D-3 for right thigh. These regions are treated horizontally along the way around the arms and legs by applying magnet or magnets in horizontal order in parallel to the subregional division lines.

Figure 3:
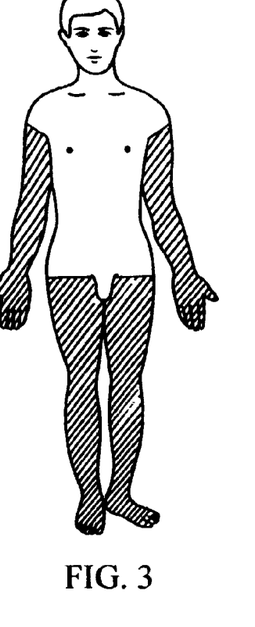
FIG. 3 is a perspective view showing the application of extremities of a person to magnet means of applying a magnet to the entire area of the extremities of a person.
Figure 6:
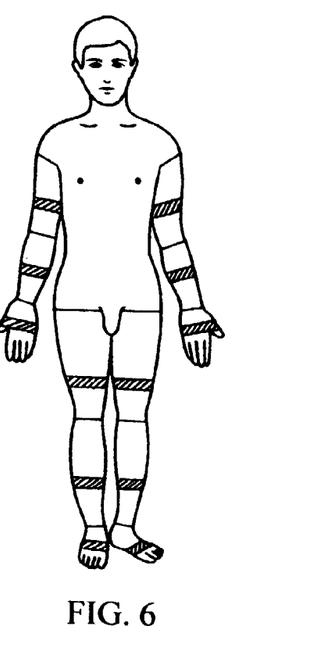
FIG. 6 is a perspective view showing the partial application of magnet means with a magnet to all subregions of the extremities of both hands, forearms, upper arms, feet, lower legs and thighs of a person together concurrently in horizontal order.
Figure 7:
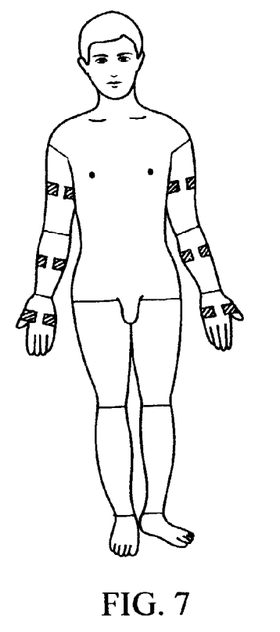
FIG. 7 is a perspective view showing the partial application of magnet means with multiple magnets to all subregions of the upper extremities of a person together concurrently in horizontal order.
Figure 8:
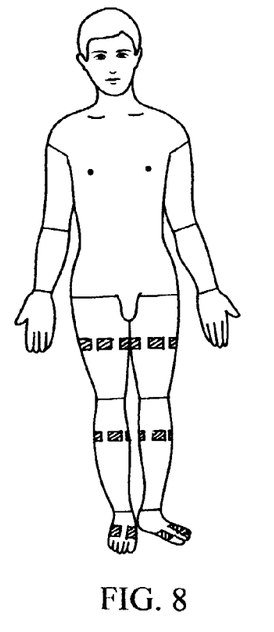
FIG. 8 is a perspective view showing the partial application of magnet means with multiple magnets to all subregions of the lower extremities of a person together concurrently in horizontal order.
Figure 9:
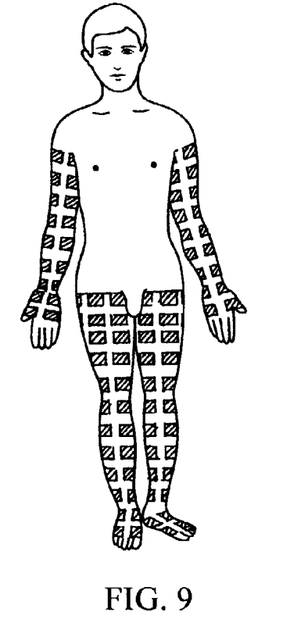
FIG. 9 is a perspective view showing a partial application of magnet means with multiple magnets to all regions of the extremities of a person together concurrently in horizontal order.
Figure 10:
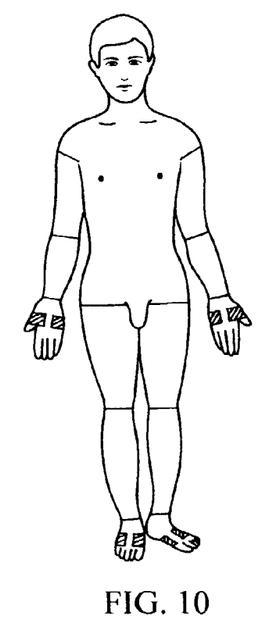
FIG. 10 is a perspective view showing the partial application of magnet means with multiple magnets to a subregion of each hand and foot of a person concurrently in horizontal order, for a balanced treatment.
Figure 11:
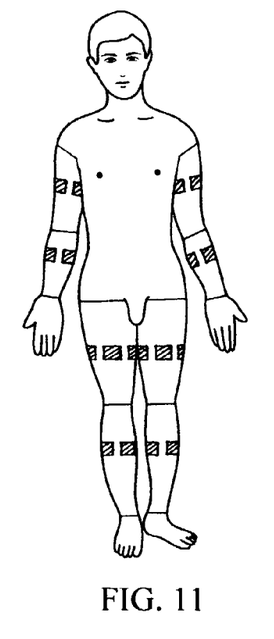
FIG. 11 is a perspective view showing the partial application of magnet means with multiple magnets to subregions of both forearms, upper arms, lower legs and thighs of a person concurrently in horizontal order, for a balanced treatment.
Figure 12:
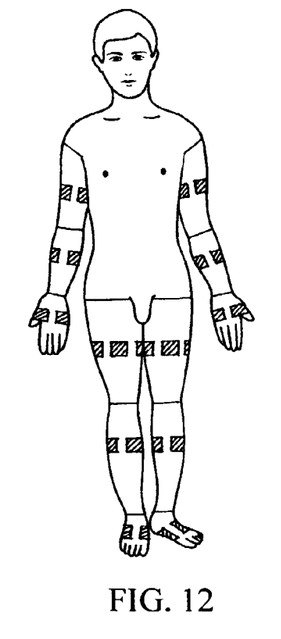
FIG. 12 is a perspective view showing the partial application of magnet means with multiple magnets to all subregions of both arms and legs of a person concurrently in horizontal order, for a balanced treatment.
Figure 13:
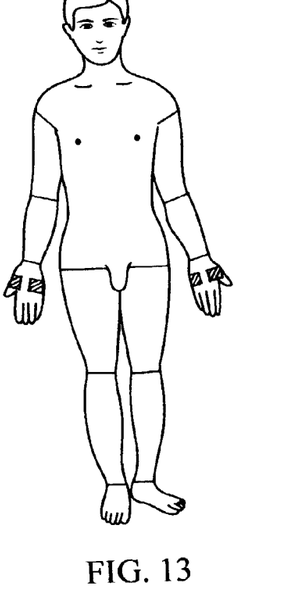
FIG. 13 is a perspective view showing the partial application of magnet means with multiple magnets to a corresponding part of a subregion of both hand of a person concurrently in horizontal order, for a balanced treatment.
Figure 14:
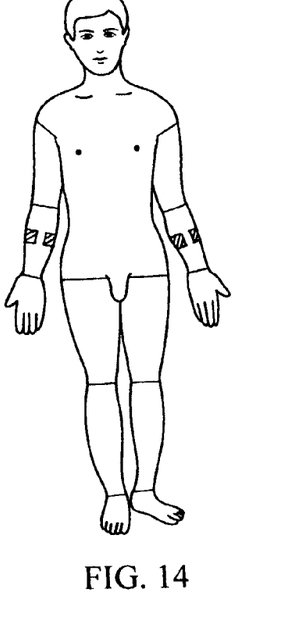
FIG. 14 is a perspective view showing the partial application of magnet means with multiple magnets to a corresponding part of a subregion of both forearms of a person concurrently in horizontal order, for a balanced treatment.
Figure 15:
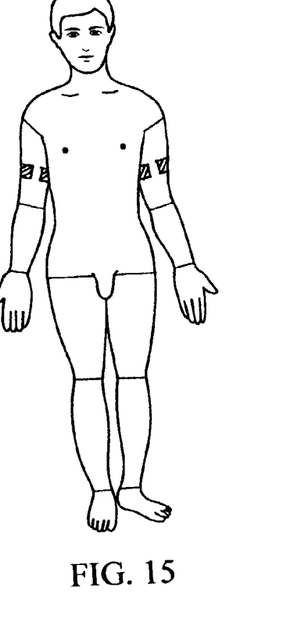
FIG. 15 is a perspective view showing the partial application of magnet means with multiple magnets to a corresponding part of a subregion of both upper arms of a person concurrently in horizontal order, for a balanced treatment.
Figure 16:
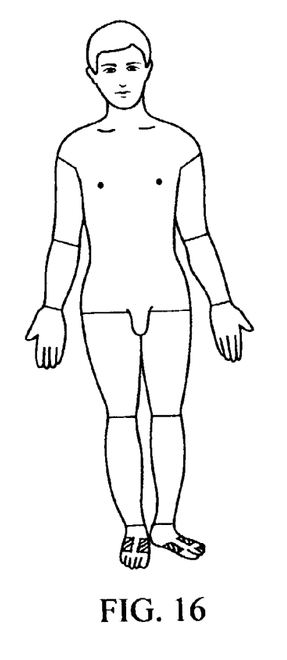
FIG. 16 is a perspective view showing the partial application of magnet means with multiple magnets to a corresponding part of a subregion of both feet of a person concurrently in horizontal order, for a balanced treatment.
Figure 17:
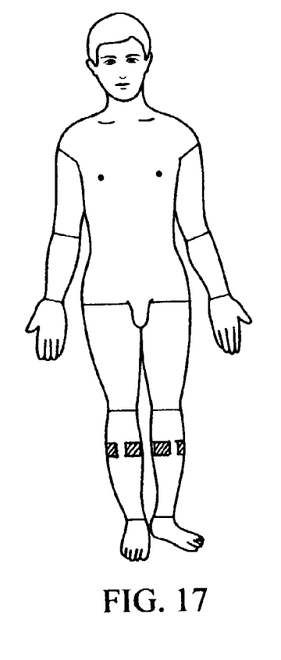
FIG. 17 is a perspective view showing the partial application of magnet means with multiple magnets to a corresponding part of a subregion of both lower legs of a person concurrently in horizontal order, for a balanced treatment.
Figure 18:
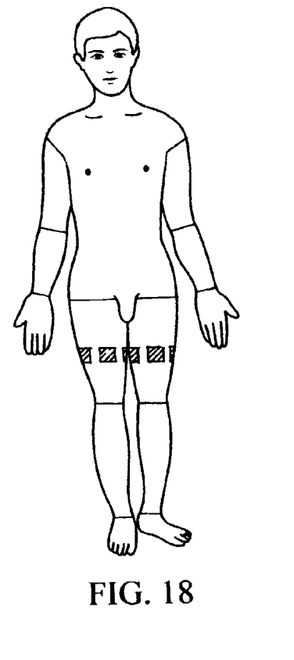
FIG. 18 is a perspective view showing the partial application of magnet means with multiple magnets to a corresponding part of a subregion of both thighs of a person concurrently in horizontal order, for a balanced treatment.
Figure 19:
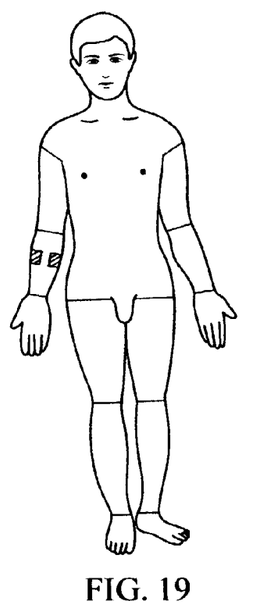
FIG. 19 is a perspective view showing the partial application of magnet means with multiple magnets to a subregion of right forearm of a person to be alternated with left forearm in the corresponding area in horizontal order.
Figure 20:
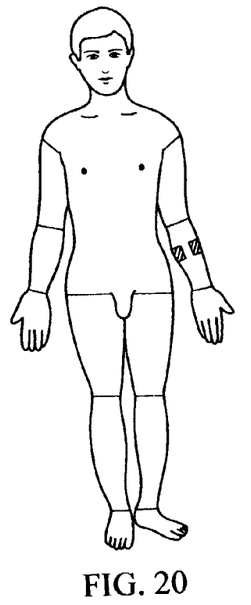
FIG. 20 is a perspective view showing the partial application of magnet means with multiple magnets to a subregion of left forearm of a person alternated by right forearm in the corresponding area in horizontal order.

Thus, all meridians disposed in the extremities of the body are affected simultaneously and equally in balance, regardless of what subregion or horizontal zone is used, and thereby afflictions of all ailments related with the arm and leg meridians and its organs are treated concurrently and holistically. All regions may be treated altogether as a whole, as shown in FIG. 3, or partially by subregions at a time independently, as shown in FIGS. 19,20,22 & 23 or partially by all regions together, as shown in FIGS. 6, 9 & 12 of the drawings. Since the body is composed with two arms and two legs in identical way in terms of the dual energy system and its meridian as well as its shape and function, a balanced application is essential and very important by which brings the system into a balance and harmony. Therefore, these subregions of the extremities are treated in pair by arm or leg either separately, or alternatively or in-group or all together as a whole, as shown in FIGS. 7, 8, 9, 12, 19, 20, 22 and 23 of the drawing. Thus, a balanced treatment effect is achieved by applying magnet means to the designated area of the extremities, and afflictions of all ailments and diseases of entire body are treated concurrently and holistically. Hence, the method utilizes both arms and legs, together as respective pair, concurrently, as shown in FIGS. 13, 14, 15, 16, 17 & 18 of the drawing. For example, if region "A-1" of left hand is applied, then region "B-1" of right hand of counter pair should also be applied alternately or together concurrently, as one pair, regardless of pain or not, for a balanced treatment, and this practice should apply in same way for lower extremities of both legs, otherwise, causes an imbalanced treatment effect such as a possible side effect or a reduced effectiveness.

The region "A-1" and "B-1" is preferably utilized when hand is in pain or ache, and the region "A-2" and "B-2" is preferably utilized when forearm is in pain or ache, and the region "A-3" and "B-3" is preferably utilized when upper arm is in pan or ache, and the region "C-1" and "D-1" is preferably utilized when foot is in pain or ache, and the region "C-2" and "D-2" is preferably utilized when lower leg is in pain or ache, and the region "C-3" and "D-3" is preferably utilized when thigh is in pain or ache. When all arms and legs are in pain, use all subregions concurrently, or just use any one or two or three regions of both arms and legs selectively or together in pair for a balanced treatment because it all produces a holistic effectiveness for the entire body. This method of extremity may be utilized with the head, neck and trunk method of prior art together or any one or two selectively and concurrently to increase effectiveness with less time of treatment which is extremely helpful especially in relieving chronic type pains in the region of hand, forearm, upper arm, foot, lower leg and thigh, and symptoms of inflammation, cramp, neuralgia, arthritis, numbness, leg/feet tiredness & heavy, hand/feet/knee cold, etc.

The method of extremity treatment by utilizing magnet or magnets are described as follows; Magnet or magnets are attached directly to the extremities in the designated area, as shown in FIGS. 3, 4, 5, 6, 7, 8, 9, 10, 11, 12, 13, 14, 15, 16, 17, 18, 19, 20, 22 and 23 of the drawings.

The magnet or magnets may be applied evenly to the entire treating area all the way around the extremities in parallel to the horizontal subregional lines, concurrently with an equal total flux, as shown in FIG. 3 of the drawings, or partially by region at a time, as shown in FIGS. 19, 20, 22 and 23 of the drawing, independently or alternatively or consecutively or at intervals, one by one with an equal total flux and an equal amount of treatment time or partially by regions in groups at a time, as shown in FIGS. 4, 5, 6, 7, 8, 10, 11, and 12 of the drawings, with an equal total flux and an equal amount of treatment time, or partially by all regions together concurrently as shown in FIG. 9 of the drawings. In utilizing partial treatment by region at a time, or regions in-group or altogether, balanced treatment should be practiced by using an equal total flux and an equal amount of treatment time. In addition, magnet or magnets should also be applied or attached to the corresponding area or part of the respective treating regions of the counter pair of the extremity for a balanced treatment effect as shown in FIGS. 13, 14, 15, 16, 17 and 18 of the drawing.

Figure 21:
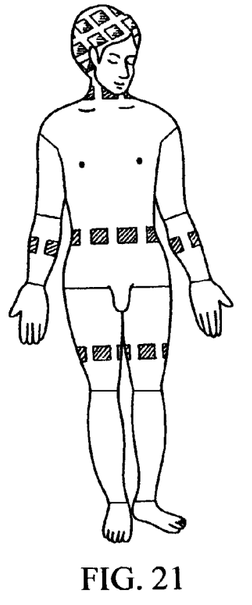
FIG. 21 is a perspective view showing a combined treatment of extremity, trunk, neck and head together concurrently.
Figure 22:
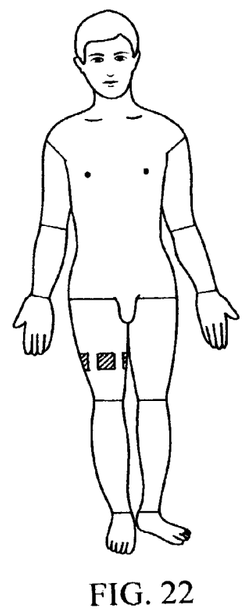
FIG. 22 is a perspective view showing the partial application of magnet means with multiple magnets to a subregion of right thigh of a person to be alternated with left thigh in the corresponding area in horizontal order.
Figure 23:
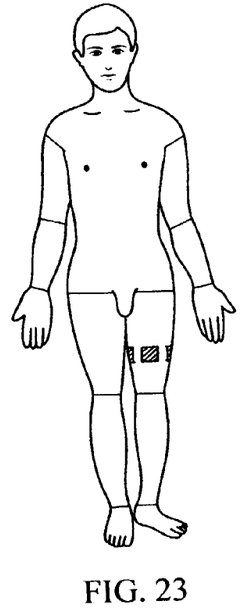
FIG. 23 is a perspective view showing the partial application of magnet means with multiple magnets to a subregion of left thigh of a person alternated by right thigh in the corresponding area in horizontal order.

Partial treatment may be practiced with any number of magnets sized more than ¹⁄₁₆" in diameter. Number of magnets used is determined by size and total flux of the magnet based on repelling and pulling power. When applying multiple magnets for partial treatment of a region or multiple regions together, magnets are placed and spaced apart one another at an equal distance through out a region or regions, in parallel with the horizontal subregional line, as shown in FIGS. 7, 8, 9, 10, 11 and 12 of the drawings, so that magnets are placed evenly around the entire area of the horizontal zones of the treating regions of the extremities. Thus, all parts of the extremities and its meridians are treated equally of total flux for balanced treatment. Also, this method can be applied together with the head, neck and trunk method of prior art, as shown in FIG. 21 of the drawing, for more effectiveness and better-balanced effect. When utilizing the combined method of the head, neck, trunk and extremities together, magnets should be applied concurrently in same way as to produce a balanced treatment effect for all regions involved with the combined method, as shown in FIG. 21, with same total flux and an equal amount of treatment time. In the case of using the combined method with trunk, neck and head, applying magnets by region consecutively at a time is not appropriate because too many meridians are involved that make difficult to achieve a balanced treatment at a time.

In applying magnetism to the extremities of a patient, the magnets are preferably configured and sized to cover partially or substantially the regional area of the extremities, and preferably to cover substantially the entire regions of the extremities of the patient. Only the North Pole of a magnet is applied. In utilizing the area in the regions in application to the extremities of a patient, it is typically and ordinarily necessary, in order to avoid a imbalance treatment in accordance with the Oriental medical theory, to apply magnet or magnets with an equal total flux for each and all treating area of the regions with an equal amount of treatment time for a balanced treatment. And, in addition, the balanced concept should also be applied by using the median line of the body that divides the extremity into a half, left and right, in order to avoid an imbalance condition of the body systems. Accordingly, when applying magnet or magnets around the extremities in parallel to the horizontal subregional division lines, always place the magnets evenly at an equal distance all the way round in the horizontal order, and use both arms or legs as respective counter pair in corresponding manner in selection of the treating regions or horizontal zone area, as shown in FIG. 7, 8, 10, 11 and 12 of the drawings, so that a balanced treatment is possible with an equal distribution of magnetic flux for each and every side of the extremities, and this practice should be applied to all magnet sizes used under this extremity method of magnetic application.

Any magnet, permanent or electromagnet, or solid or flexible, may be utilized.

Typically, a flat magnet is employed, thus to provide well contact and substantially equal magnetic flux over the area of the extremities. In applying magnets to the extremities of a patient, it is desirable that magnets of equal size and total flux are applied evenly to whole area of the extremities and, in addition, for treatment partially by subregion of the extremities together, equal time of treatment should be practiced for a balanced treatment.

The magnet may have any configuration appropriate to the area to which it is to be applied, such as square, rectangular, circular, oval, disc, bar or flexible. The size of the magnet should be such as to cover the entire regions of the extremities or only the subregions of the extremities or only a part of the subregions, at least more than ¹⁄₁₆" inch diameter. Practically, any size appropriate for the extremities is usable, however, the range of the magnet size preferred for this extremity method is from ¹⁄₁₆"×¹⁄₁₆" to 20"×45". Any magnet within this range of size can be effectively used.

Figure 24:
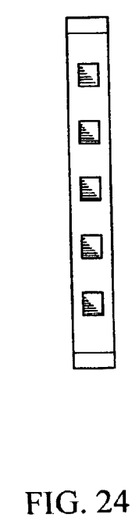
FIG. 24 is a perspective view showing a wrap around style band, utilized for a partial treatment of a region or regions of the extremities of a person concurrently with multiple magnets, made of elasticized material with Velcro fasteners for the application of a north pole of a magnet of rectangular configuration to the extremities of arms and legs of a person.

In applying magnet means to the extremities, magnet or magnets are attached to the extremity skin in the designated area of the extremities by using elastic band, wrapper or cover, appropriate for the shape of extremities, with Velcro fasteners for well contact, as shown in FIG. 24 of the drawings.

Elastic band may include wraparound belts to securely hold the magnets sewn-in or encased in fabric lining, or adjustable Velcro type fasteners. The magnet is positioned so that it is not readily removable or separable from the skin of the extremities of the patient in order to be properly effective.

Magnets should be contacted well to the skin of the extremities so that no gab between magnet and skin is allowed. As disclosed in the prior art of the two-hand and the head method, the closer contact to the skin for magnet the better for effectiveness and, on the contrary, the farther from the skin the lesser effective.

The method is applicable for all afflictions, ailments and diseases associated with the extremities and its meridians. As stated, the method is extremely effective according to the invention, and serves to treat concurrently various or all afflictions and ailments of the entire body of a person. The method also serves to energize the person and relieve tiredness.

Effectiveness and applicability of the method are all observable at treatment site and easily verifiable instantly by patient during treatment in same way as prior art of two-hand and the head magnetic method.

Treatment may begin with a relatively low power magnet, with successive application of magnets of increasing strength in accordance with the progress, response and feeling of the patient relative to relief. Typically, response is felt after 15 minutes, and within 30 minutes the patient can sense a cure in progress and a good feeling. Fifteen to ninety minutes of application is the optimum period for most effective treatment of most ailments or diseases. The treatment time is typically 15 to 180 minutes, typically once or twice daily at interval of about 10 hours.

The north side of the magnet is applied directly to the area of the extremities and is left in place for 15 to 180 minutes. Pain is typically then gone.

Treatment commences upon application of the magnet and typically extends from 15 to 180 minutes, one or two times per day, at intervals of about 10 hours.

At the end of each treatment, the magnet or magnets are removed. Most ailments or diseases are cured or greatly alleviated with one or two treatments. Treatment may be repeated until complete cure is affected. The treatment may be repeated at intervals in accordance with need and progress. For relatively serious or long-term ailments, treatment may extend for many days, and even for a few months or more. The effectiveness of treatment extends for about four to ten hours after removal of the magnet or magnets. Relatively simple or minor ailments or complaint is cured with one or two treatment.

The criterion used in this invention for therapeutic effectiveness and operativeness was "Did all pains of patient relieved concurrently from whole body within 15 minutes to two hour of each treatment session and did any side effect occurred or accompanied and did patient detect ailment and progress of cure and did patient feel energized".

Applying North Pole of the magnet to the designated area of the extremities of the patients, in accordance with the invention, relieves all pains of whole body concurrently, regardless of cause and location, showing holistic total effect for whole body of the patient. Of various medical treatments, utilizing magnet means to the extremities in accordance with the invention is found to be very effective to cope with pains and affliction. In practice of this holistic treatment, cause, location and names of ailments involved are not considered as important factors for treatment because all pains and afflictions associated with various ailments of whole body including chronic diseases are treated holistically and concurrently with excellent result of pain relief and cure, which are all observable and verifiable at site while treated within 15 minutes to three hours with no waiting time period for the treatment result, unlike conventional method.

And in addition, patients can detect own ailments and cure in progress and final result as well by symptoms occurred in response to the magnetic application to the extremities, and patients treated become energized and feel a power or strength in arms and wrists, especially when awaked in the morning.

Introduced below shows a typical example of the holistic total treatment for afflictions of all ailments of entire body for which the magnet device and the method were utilized—male patient, 69 years old, suffering from constant pain symptoms of arthritis of wrist, finger joints and left knee and lumbago, cystitis, stomachache/chest-heartburn and neuralgia for many years, was treated with this extremity method by utilizing 32 magnets of 1"D×0.751T" with about 5,000 total flux per magnet for one or two times every day. The pain symptoms were relieved holistically every time treated and the overall pain symptoms were substantially relieved with about two month treatments, which is a remarkable result. The patient was able to live normal life in free of pain. Normally, it is impossible to cure or manage such symptoms in two month with the conventional method.

Figure 4:
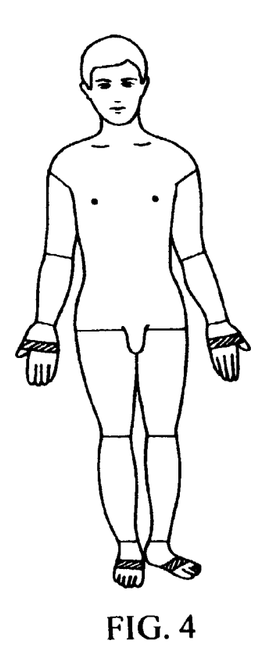
FIG. 4 is a perspective view showing the partial application of magnet means with a magnet to subregions of the extremities of both hands and feet of a person together concurrently in horizontal order.
Figure 5:
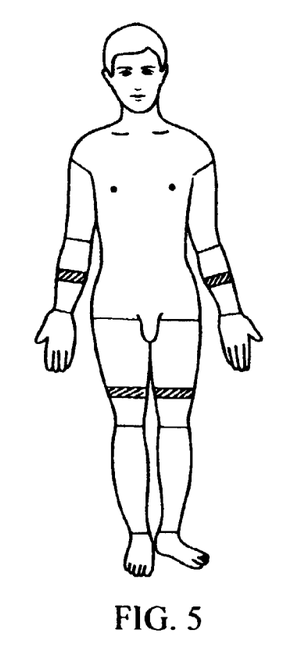
FIG. 5 is a perspective view showing the partial application of magnet means with a magnet to subregions of the extremities of both forearms and thighs of a person concurrently in horizontal order.

In proceeding according to the invention, the person or patient is preferably in a prone position, or seated position for the application of magnetism. Magnet means may be applied to the extremities while the person is in a standing, as indicated in FIGS. 4, 5 and 6, or sitting, or recline position.

During the treatment, afflictions, ailments and diseases of a person are detected and sensed by the responses and symptoms of the person in response to the application of the magnetism in same way as prior art of two-hand and head magnetic method. The patient may sense responses involving complex symptoms, such as pain, strain, tightness, itch, warmth, coldness, etc.

Such symptoms may be mixed and continue until the spot is cured or relieved. The patient may sense cure in progress during the application of magnetism in accordance with the invention.

The response or reaction of the patient to the extremity treatment may involve the entire body. Symptoms occur from all diseased or afflicted areas of the body of the patient, and symptoms are usually continued until all ailments and diseases are greatly alleviated or cured. When all ailments are cured, all symptoms and responses are completely gone and this happens only when there is no ailment in the body. Thus there is no symptom or response occurring from healthy body even under magnetic application to the head or hands. Such phenomenon is all observable and verifiable instantly by patient at treatment site while in treatment. As stated earlier, after application of the magnet for an appropriate time, the patient senses a response and therapeutical effect of cure in progress. For internal illnesses or ailments or chronic diseases, after 15 minutes of application of the magnets to the extremities, a response or reaction occurs in the patient, and the patient can sense a good response and active curing in 15 to 60 minutes of treatment. After approximately 90 minutes of application of the magnet, the response or reaction of the person's body gradually diminishes, the patient's body becomes relaxed, and a feeling of well-being permeates the patient's body. This point in time of a treatment may be called as a balanced treatment point. When balanced point is reached through the course of a treatment whole body becomes relaxed and then all pains and afflictions are gone with a feeling of well-being. At this very moment treatment should be stopped immediately—magnets should be removed from the extremity skin, otherwise, the balance point may be reversed by over-treatment with a result of less effectiveness and a possible side effect.

Therefore, in accordance with the balance concept of Oriental medical theory, the point of being relaxed, easy state of human body occurring during a treatment is believed to be the exact point of a well balanced state of harmony in body systems in treatment. The magnet may typically be applied for 15 to 180 minutes and for not more than 180 minutes of a maximum balanced point, in order to prevent over-balanced treatment. Such balanced point in treatment is also dependent upon and is affected by factors including total flux, distance between magnet and skin, and condition of ailment and thereby each person might have a different balanced point.

However, in most cases, the balance points of treatment are within a range of 15 to 180 minutes. Therefore, the magnets may be applied within the specified time period needed to produce therapeutic effect and the following schedule may preferably be observed in the extremity treatment:

| | |
|---|---|
| Treatment: | 15–180 minutes |
| Resting time: | 10 hours |
| Frequency: | 1–2 times daily or whenever pain occurs |

In application of magnetism to the extremities of person, virtually all magnet, permanent and electromagnet, including weak magnets may be used and are all effective, whereas only relatively strong magnets with a total flux of more than 5,000 are utilized in the referenced prior art of two-hand method. Permanent magnets are preferred for economic reasons, but electromagnets can be utilized to advantage because their power can be varied or desired, within design limitations. The range of total flux for magnets used is about 30–250,000 and such total flux is measured at 0.001" from the North Pole surface of the magnet means. The size of the magnet may typically be 1/16"×1/16" to 20"×45."

The effectiveness and curative results increase with increase of flux density (gauss) and total flux of the magnet applied to the person. The total flux applied to the patient is considered to be of key importance. The following formula sets forth the relationship between total flux, flux density and magnet pole area:

$\phi = BA$

Where: $\phi$ = total flux

B = flux density in gauss

A = area

Magnetic application to the extremities has been found to be very safe, however, only for precaution; magnets should not be utilized in treating infants, pregnant women and person with heart pacemaker or metal implanted.

Thus there has been shown and described a novel treatment of afflictions and ailments with magnetism which fulfills all the objects and advantages sought therefore. Many changes, modifications, variations and other uses and applications of the subject invention will, however, become apparent to those skilled in the art after considering this specification together with the accompanying drawings and claims.

All such changes, modifications, variations and other uses and applications which do not depart from the spirit and scope of the invention are deemed to be covered by the invention which is limited only by the claims which follow.

The invention claimed is:

1. A method of treating and alleviating human afflictions, ailments and diseases holistically by application of magnetism to a plurality of treating regions of the upper extremities of both arms of a person being treated, the method comprising the steps of:
   providing magnet means having at least one North Pole surface adapted for application to the plurality of treating regions of the extremities;
   designating at least six treating regions of the upper extremities of both arms having a total size of about 990 square inches, about 495 square inches for each arm, covering an arm region from the finger tip line to the shoulder line in about 15" round and 33" long, said treating regions being divided into at least three sub-regions per arm, according to shape of the arm;
   applying said at least one North Pole surface of the magnet to at least one of the plurality of treating regions of the arm, the magnet having a size and a shape appropriate to cover at least part of one of the treating regions of the arm; and
   maintaining the magnet in contact with at least one of the treating regions of the arm for a period of 15 to 180 minutes to treat and relieve afflictions, wherein a total flux of the magnet applied to the at least one of the treating regions of the arm is in a range from about $30\phi$–$250,000\phi$.

2. The method of claim 1, further including the step of repeating the application of the magnet means for at least one additional period of time.

3. The method of claim 1, further comprising repeating the time period for treatment at least once in a 24 hour period in an interval of about 2–10 hours in accordance with treatment progress.

4. The method of claim 1, further including:
   utilizing the magnet means of the arm together with a second magnet means for treating a head, neck and body trunk of the person concurrently, or selectively.

5. The method of claim 4, further including applying the magnet means partially to at least one region of the said treating regions of the arm of the person and applying the second magnet means partially to one region of the treating regions of the head, neck and trunk of the person concurrently, or selectively.

6. The method of claim 4, further including applying the magnet means partially to multiple of said plurality of treating regions of the arm of the person and applying the second magnet means partially to multiple of plurality of treating regions of the head, neck and trunk of the person concurrently, or selectively.

7. The method of claim 4, further including applying the magnet means partially to all of said treating regions of the arm and applying the second magnet means to all treating regions of the head, neck and trunk of the person concurrently, or selectively.

8. The method of claim 4, further including the total flux of a magnet or magnets applied to each one of the pluralities of said treating regions of the arm, head, neck and trunk of the person is substantially equal.

9. The method of claim 1, further including:
   applying the magnet means alternately to one of the treating regions of the arm of the person and then applying the magnet means to one of the treating regions of other arm of the person with equal time periods for balanced treatment.

10. The method of claim 1, wherein:
the plurality of treating regions of the arm include a hand region, forearm region and upper arm region, and further including applying the magnet means to each of the plurality of treating regions of the arm.

11. The method of claim 1, further including applying the magnet means to each of the plurality of treating regions of the arm is performed in the order of the hand region, the forearm region and the upper arm region, or in reverse order.

12. The method of claim 1, further including applying the magnet means first to one selected area of the treating regions of the arm of the person and then applying the magnet means to another selected area of the treating regions of the arm of the person.

13. The method of claim 1, further including applying the magnet means first to one selected region of the plurality of treating regions of the arm of the person and then applying the magnet means to the identical region of the plurality of treating regions of the other arm of the person in identical manner for a balanced treatment.

14. The method of claim 1, further including applying the magnet means to at least one of the plurality of treating regions of the arm of the person.

15. The method of claim 1, further including applying the magnet means to multiple of said plurality of treating regions of the arm of the person concurrently.

16. The method of claim 1, further including applying the magnet means to all of said plurality of treating regions of the arm of the person concurrently.

17. The method of claim 1, further including applying the magnet means partially to at least one of the plurality of treating regions of the arm of the person concurrently.

18. The method of claim 1, further including applying the magnet means partially to multiple of said plurality of treating regions of the arm of the person concurrently.

19. The method of claim 1, further including applying the magnet means partially to all of said treating regions of the arm of the person concurrently.

20. The method of claim 1, wherein the total flux of a magnet or magnets applied to each one of the said pluralities of treating regions of the arm of the person is substantially equal.

21. The method of claim 1, further comprising applying a magnet or magnets to the treating region or regions of the arm concurrently by disposing the magnet or magnets in horizontal order all the way around the arm in parallel to the subregional division lines so that all the arm meridians are treated simultaneously and equally in balance.

22. The method of claim 1, further comprising applying multiple magnets to the treating region or regions concurrently by disposing the magnets evenly, spaced apart at an equal distance throughout the regions of the arm so that all parts of the treating regions of the arm of the person are treated equally with total magnetic flux for a balanced treatment.

23. The method of claim 1, further comprising applying additional magnets having substantially equal total flux to the treating regions of the arm of the person for a balanced treatment.

24. The method of claim 1, further comprising applying the magnet consecutively or at intervals to selected treating regions of the arm of the person for equal time periods for a balanced treatment.

25. The method of claim 1, further comprising applying the magnet means partially to each of the plurality of treating regions of the arm of the person for equal time periods for a balanced treatment.

26. The method of claim 1, further comprising applying the magnet means partially to the entire plurality of treating regions of the arm of the person for equal time periods for a balanced treatment.

27. The method of claim 1, further comprising substantially covering the entire plurality of treating regions of the arm of the person with the North Pole surface of the magnet.

28. The method of claim 1, further comprising substantially covering each of the plurality of treating regions of the arm of the person with the North Pole surface of the magnet.

29. The method of claim 1, further comprising partially covering the entire plurality of treating regions of the arm of the person with the North Pole surface of the magnet.

30. The method of claim 1, further comprising partially covering each of the plurality of treating regions of the arm of the person with the North Pole surface of the magnet.

31. The method of claim 1, further including:
disposing retaining means for holding the magnet to the arm to provide effective contact of the north pole surface of the magnet with the upper extremity.

32. The method of claim 1, further including maintaining contact of the magnet for a time period sufficient for the person to produce a mitigation or relief of pain symptoms from ailing parts of the body.

33. The method of claim 1, further including:
contacting the magnets directly to the treating regions of the arm by using a band, a wrapper or a cover with magnets sewn-in or encased in any shape of form appropriate to fit the treating regions of the upper extremities of the person.

34. The method of claim 33, wherein the band, wrapper or cover for contacting the magnets to the treating regions of the arm of the person are made with any material that is safe to the arm and appropriate for fabrication.

35. The method of claim 1, further including:
utilizing the magnet means of the arm together with a second magnet means of the leg of the person concurrently, or selectively.

36. The method of claim 35, further including applying the magnet means partially to at least one region of the said treating regions of the arm of the person and applying the second magnet means partially to one region of the treating regions of the leg of the person concurrently, or selectively.

37. The method of claim 35, further including applying the magnet means partially to multiple of said plurality of treating regions of the arm and applying the second magnet means partially to multiple of plurality of treating regions of the leg of the person concurrently, or selectively.

38. The method of claim 35, further including applying the magnet means to all of said treating regions of the arm of the person and applying the second magnet means to all treating regions of the leg of the person concurrently, or selectively.

39. The method of claim 35, further including the total flux of a magnet or magnets applied to each one of the pluralities of said treating regions of the arm and leg of the person is substantially equal.

40. The method of claim 35, further including the total flux of a magnet or magnets applied to each area of the plurality of said treating regions of the arm and leg of the person is substantially equal.

41. The method of claim 1, further including the magnet having a size of 1/16"×1/16" to 15"×33" and a shape appropriate to cover at least part of one of the treating regions of the arm of the person.

42. The method of claim 1, further including a total flux of the magnet applied to the at least one of the treating regions of the arm is in a range from about 10ϕ–250,000ϕ.

43. A method of treating and alleviating human afflictions, ailments and diseases holistically by application of magnetism to a plurality of treating regions of the lower extremities of both legs of a person being treated, the method comprising the steps of:
providing magnet means having at least one North Pole surface adapted for application to the plurality of treating regions of the extremities;
designating at least six treating regions of the lower extremities of two legs having a total size of about 1,800 square inches, about 900 square inches for each leg, covering a leg region from a toe line to the buttocks line in about 20" round and 45" long, said treating regions being divided into at least three sub-regions per leg, according to shape of the leg;
applying said at least one North Pole surface of the magnet to at least one of the plurality of treating regions of the leg, the magnet having a size and shape appropriate to cover at least part of one of the treating regions of the leg; and
maintaining the magnet in contact with at least one of the treating regions of the leg for a period of 15 to 180 minutes to treat and relieve afflictions, wherein a total flux of the magnet applied to the at least one of the treating regions of the leg is in a range from about 30ϕ–250,000ϕ.

44. The method of claim 43, further including the step of repeating the application of the magnet means for at least one additional period of time.

45. The method of claim 43, further comprising repeating the time period for treatment at least once in a 24 hour period in an interval of about 2–10 hours in accordance with treatment progress.

46. The method of claim 43, further including:
utilizing the magnet means of the leg together with a second magnet means for treating an arm, head, neck and body trunk of a person concurrently, or selectively.

47. The method of claim 46, further including applying the magnet means partially to at least one region of the said treating regions of the leg of the person and applying the second magnet means partially to one region of the treating regions of the arm, head, neck and trunk of the person concurrently, or selectively.

48. The method of claim 46, further including applying the magnet means partially to multiple of said plurality of treating regions of the leg and applying the second magnet means partially to multiple of plurality of treating regions of the arm, head, neck and trunk of the person concurrently, or selectively.

49. The method of claim 46, further including applying the magnet means partially to all of said treating regions of the leg and applying the second magnet means to all treating regions of the arm, head, neck and trunk of the person concurrently, or selectively.

50. The method of claim 46, further including the total flux of a magnet or magnets applied to each one of the pluralities of said treating regions of leg, arm, head, neck and trunk of the person is substantially equal.

51. The method of claim 43, further including: applying the magnet means alternately to one of the treating regions of the leg of the person and then applying the magnet means to one of treating regions of other leg of the person with equal time periods for balanced treatment.

52. The method of claim 43, wherein:
the plurality of treating regions of the leg include a foot region, lower leg region and thigh region, and further including applying the magnet means to each of the plurality of treating regions of the leg.

53. The method of claim 43, further including applying the magnet means to each of the plurality of treating regions of the leg is performed in the order of the foot region, the lower leg region and the thigh region, or in reverse order.

54. The method of claim 43, further including applying the magnet means first to one selected area of the treating regions of the leg of the person and then applying the magnet means to other selected area of the treating regions of the leg of the person.

55. The method of claim 43, further including applying the magnet means first to one selected region of the plurality of treating regions of the leg of the person and then applying the magnet means to the identical region of the plurality of treating regions of the other leg of the person in identical manner for a balanced treatment.

56. The method of claim 43, further including applying the magnet means to at least one of the plurality of treating regions of the leg of the person.

57. The method of claim 43, further including applying the magnet means to multiple of said plurality of treating regions of the leg of the person concurrently.

58. The method of claim 43, further including applying the magnet means to all of said plurality of treating regions of the leg of the person concurrently.

59. The method of claim 43, further including applying the magnet means partially to at least one of the plurality of treating regions of the leg of the person concurrently.

60. The method of claim 43, further including applying the magnet means partially to multiple of said plurality of treating regions of the leg of the person concurrently.

61. The method of claim 43, further including applying the magnet means partially to all of said treating regions of the leg of the person concurrently.

62. The method of claim 43, wherein the total flux of a magnet or magnets applied to each one of the said pluralities of treating regions of the leg of the person is substantially equal.

63. The method of claim 43, further comprising applying magnet or magnets to the treating region or regions of the leg concurrently by disposing the magnet or magnets in horizontal order all the way around the leg in parallel to the sub regional division lines so that all the leg meridians are treated simultaneously and equally in balance.

64. The method of claim 43 further comprising applying multiple magnets to the treating region or regions concurrently by disposing the magnets evenly, spaced apart at an equal distance throughout the regions of the leg so that all parts of the treating regions of the leg of the person are treated equally with total magnetic flux for a balanced treatment.

65. The method of claim 43, further comprising applying additional magnets having substantially equal total flux to the treating regions of the leg of the person for a balanced treatment.

66. The method of claim 43, further comprising applying the magnet consecutively or at intervals to selected treating regions of the leg of the person for equal time periods for a balanced treatment.

67. The method of claim 43, further comprising applying the magnet means partially to each of the plurality of treating regions of the leg of the person for equal time periods for a balanced treatment.

68. The method of claim 43, further comprising applying the magnet means partially to the entire plurality of treating regions of the leg of the person for equal time periods for a balanced treatment.

69. The method of claim 43, further comprising substantially covering the entire plurality of treating regions of the leg of the person with the North Pole surface of the magnet.

70. The method of claim 43, further comprising substantially covering each of the plurality of treating regions of the leg of the person with the North Pole surface of the magnet.

71. The method of claim 43, further comprising partially covering the entire plurality of treating regions of the leg of the person with the North Pole surface of the magnet.

72. The method of claim 43, further comprising partially covering each of the plurality of treating regions of the leg of the person with the North Pole surface of the magnet.

73. The method of claim 43, further including:
disposing retaining means for holding the magnet to the leg to provide effective contact of the North Pole surface of the magnet with the lower extremity.

74. The method of claim 43, further including maintaining contact of the magnet for a time period sufficient for the person to produce a mitigation or relief of pain symptoms from ailing parts of the body.

75. The method of claim 43, further including:
contacting the magnets directly to the treating regions of the leg by using a band, a wrapper or a cover with magnets sewn-in or encased in any shape of form appropriate to fit the treating regions of the lower extremities of the person.

76. The method of claim 75, wherein the band, wrapper or cover for contacting the magnets to the treating regions of the leg of the person are made with any material that is safe to the leg and appropriate for fabrication.

77. The method of claim 43, further including a total flux of the magnet applied to the at least one of the treating regions of the leg is in a range from about $10\phi$–$25,000\phi$.

78. The method of claim 43, further including the magnet having a size of $1/16"\times1/16"$ to $20"\times45"$ and a shape appropriate to cover at least part of one of the treating regions of the leg of the person.

* * * * *